United States Patent
Schabbach et al.

(10) Patent No.: US 10,881,805 B2
(45) Date of Patent: * Jan. 5, 2021

(54) DRUG DELIVERY DEVICE AND METHOD FOR A DRUG DELIVERY DEVICE

(71) Applicant: Sanofi-Aventis Deutschland GMBH, Frankfurt am Main (DE)

(72) Inventors: Michael Schabbach, Frankfurt am Main (DE); Graham Jay, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 48 days.

This patent is subject to a terminal disclaimer.

(21) Appl. No.: 16/258,995

(22) Filed: Jan. 28, 2019

(65) Prior Publication Data

US 2019/0151556 A1 May 23, 2019

Related U.S. Application Data

(63) Continuation of application No. 15/350,587, filed on Nov. 14, 2016, now Pat. No. 10,226,580, which is a
(Continued)

(30) Foreign Application Priority Data

Nov. 12, 2010 (EP) ..................................... 10190936

(51) Int. Cl.
*A61M 5/315* (2006.01)
*A61J 1/20* (2006.01)
(Continued)

(52) U.S. Cl.
CPC ........ *A61M 5/31535* (2013.01); *A61J 1/2093* (2013.01); *A61M 5/2066* (2013.01);
(Continued)

(58) Field of Classification Search
CPC ............ A61M 5/31535; A61M 5/2066; A61M 5/2448; A61M 5/1684; A61M 2205/3306; A61M 2205/587; A61J 1/2093
See application file for complete search history.

(56) References Cited

U.S. PATENT DOCUMENTS 533,575 A 2/1895 Wilkens
3,352,779 A 11/1967 Austin
(Continued)

FOREIGN PATENT DOCUMENTS

EP 0937471 8/1999
EP 0937476 8/1999
(Continued)

OTHER PUBLICATIONS

International Preliminary Report on Patentability in International Application No. PCT/EP2011/069815, dated May 14, 2013, 9 pages.
(Continued)

*Primary Examiner* — Nathan R Price
*Assistant Examiner* — Melissa A Snyder
(74) *Attorney, Agent, or Firm* — Fish & Richardson P.C.

(57) ABSTRACT

A drug delivery device is provided comprising a container, a first product and a second product. The device is configured to mix the first product and the second product with each other within the container for forming a drug mixture. The device is further configured for dispensing the drug mixture. The device comprises a mixing member. The device is switchable from a first state, in which the first product and the second product are separated, into a second state, in which the first product and the second product are mixed. The mixing member is configured to exert a force onto the container in order to move the container to mix the first product and the second product with each other. Fur-
(Continued)

thermore, a method for maintaining a predetermined property of a drug mixture to be dispensed from a drug delivery device is provided.

18 Claims, 7 Drawing Sheets

Related U.S. Application Data continuation of application No. 13/883,391, filed as application No. PCT/EP2011/069815 on Nov. 10, 2011, now Pat. No. 9,492,620.

(60) Provisional application No. 61/438,406, filed on Feb. 1, 2011.

(51) Int. Cl.
| | | |
|---|---|---|
| *A61M 5/20* | (2006.01) | |
| *A61M 5/24* | (2006.01) | |
| *A61M 5/31* | (2006.01) | |
| A61M 5/168 | (2006.01) | |
| G06F 19/00 | (2018.01) | |
| G16H 20/13 | (2018.01) | |

(52) U.S. Cl.
CPC ........ *A61M 5/2448* (2013.01); *A61M 5/3129* (2013.01); *A61M 5/3146* (2013.01); *A61M 5/31541* (2013.01); *A61M 5/31596* (2013.01); A61M 5/1684 (2013.01); A61M 2005/2485 (2013.01); A61M 2205/3306 (2013.01); A61M 2205/3389 (2013.01); A61M 2205/587 (2013.01); G06F 19/3462 (2013.01); G16H 20/13 (2018.01)

(56) References Cited

U.S. PATENT DOCUMENTS

| | | | |
|---|---|---|---|
| 5,226,895 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,171,276 | B1 | 1/2001 | Lippe et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,793,646 | B1 | 9/2004 | Giambattista et al. |
| 6,899,698 | B2 | 5/2005 | Sams |
| 6,915,823 | B2 | 7/2005 | Osborne et al. |
| 6,936,032 | B1 | 8/2005 | Bush, Jr. et al. |
| 7,241,278 | B2 | 7/2007 | Moller |
| 9,492,620 | B2 | 11/2016 | Schabbach et al. |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0150712 | A1* | 7/2006 | Berstis ............ A61M 16/10 73/23.2 |
| 2006/0153693 | A1 | 7/2006 | Fiechter et al. |
| 2009/0275916 | A1 | 11/2009 | Harms et al. |
| 2009/0299328 | A1 | 12/2009 | Mudd et al. |
| 2010/0211005 | A1 | 8/2010 | Edwards et al. |

FOREIGN PATENT DOCUMENTS

| | | |
|---|---|---|
| EP | 1518575 | 3/2005 |
| EP | 1923083 | 5/2008 |
| WO | WO 99/38554 | 8/1999 |
| WO | WO 01/10484 | 2/2001 |

OTHER PUBLICATIONS

International Search Report and Written Opinion for International Application No. PCT/EP2011/069815, dated Feb. 14, 2012, 11 pages.

Oxford Dictionary [online], "Sensor," retrieved on Jan. 15, 2018, from: URL <https://en.oxforddictionaries.com/definition/sensor>, 1 page.

Wikipedia [online], "Physical Property," Feb. 2003, retrieved on Feb. 14, 2018 from: URL <https://wikipedia.org/w/index.php?title=Physical_property&oldid-39872444>, 3 pages.

* cited by examiner

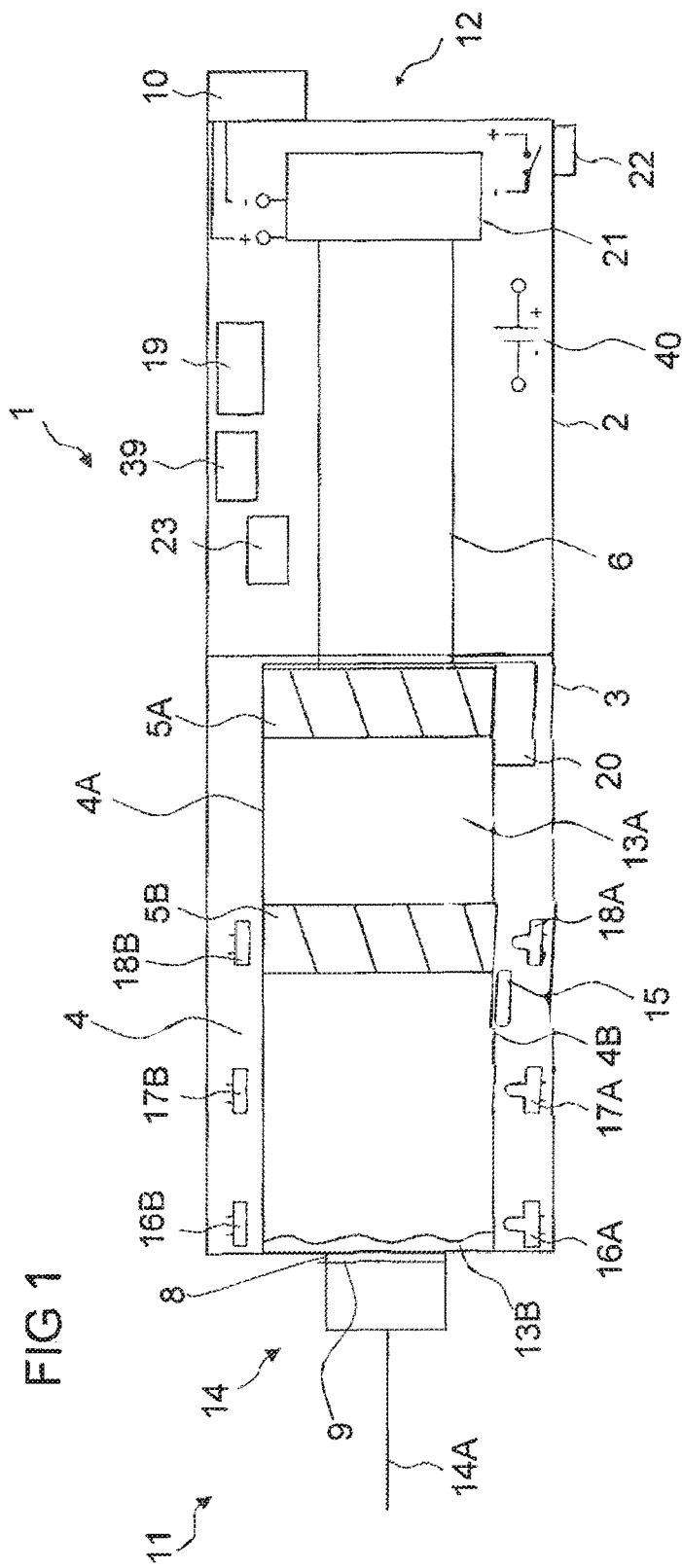

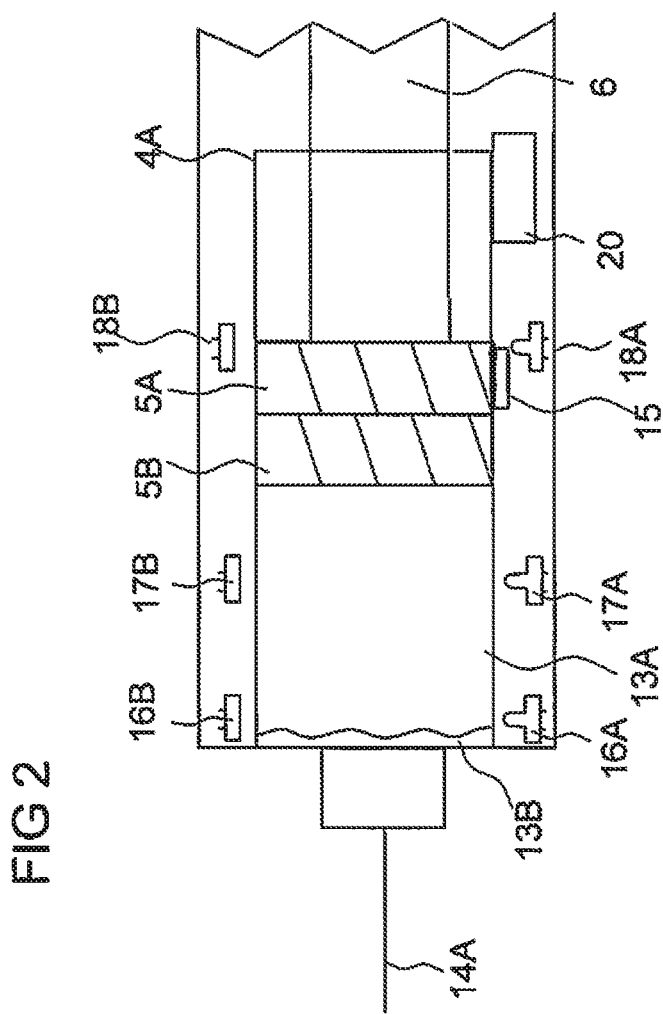

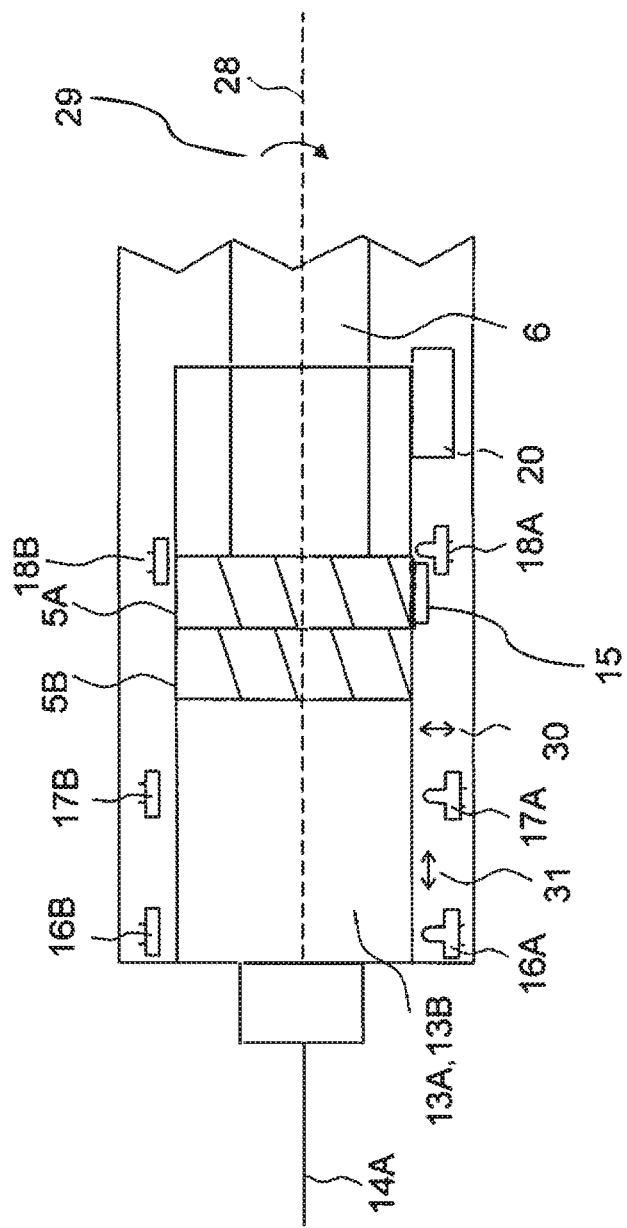

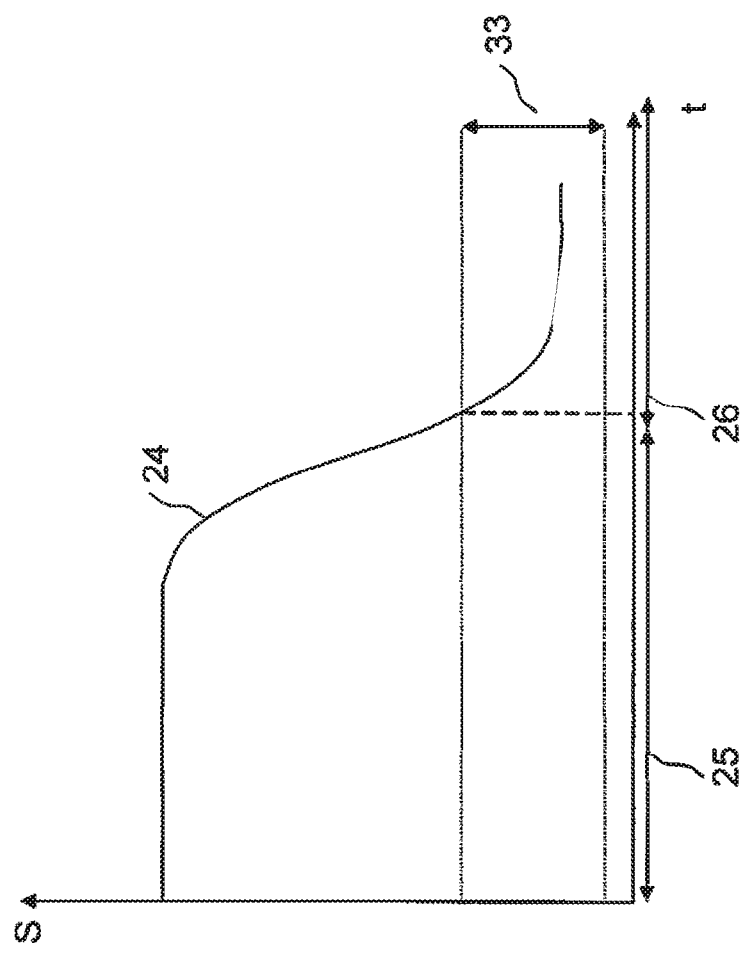

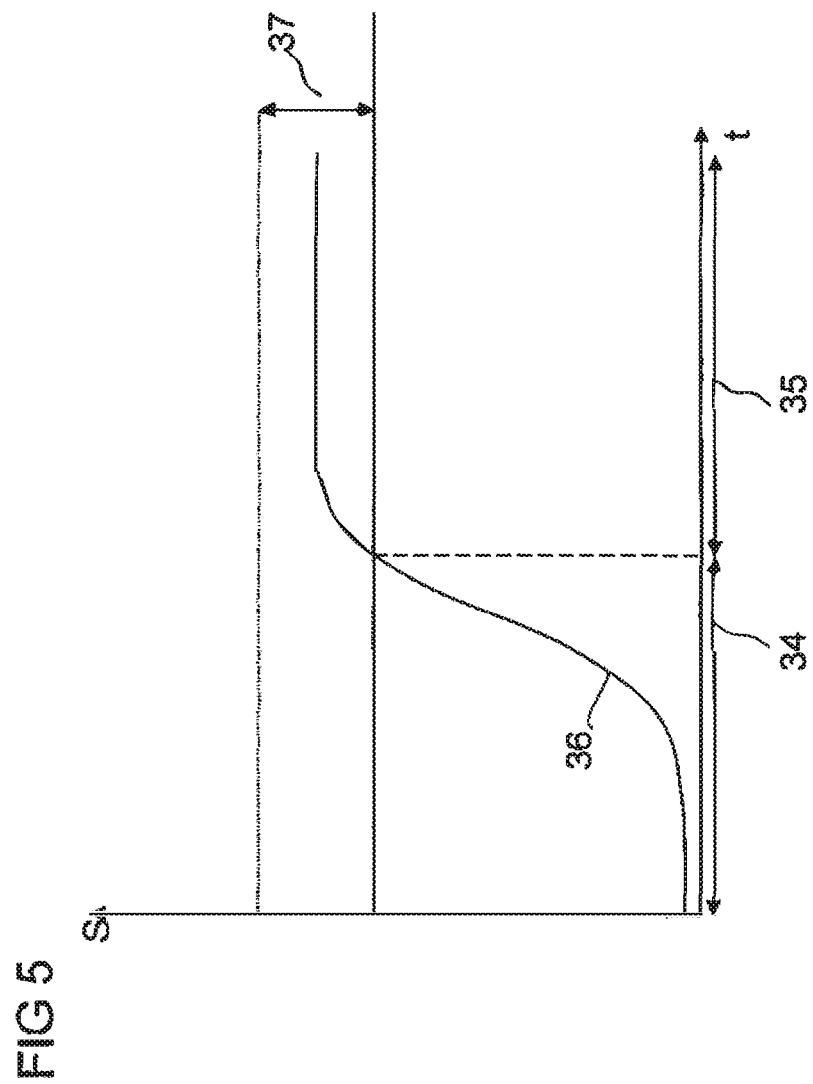

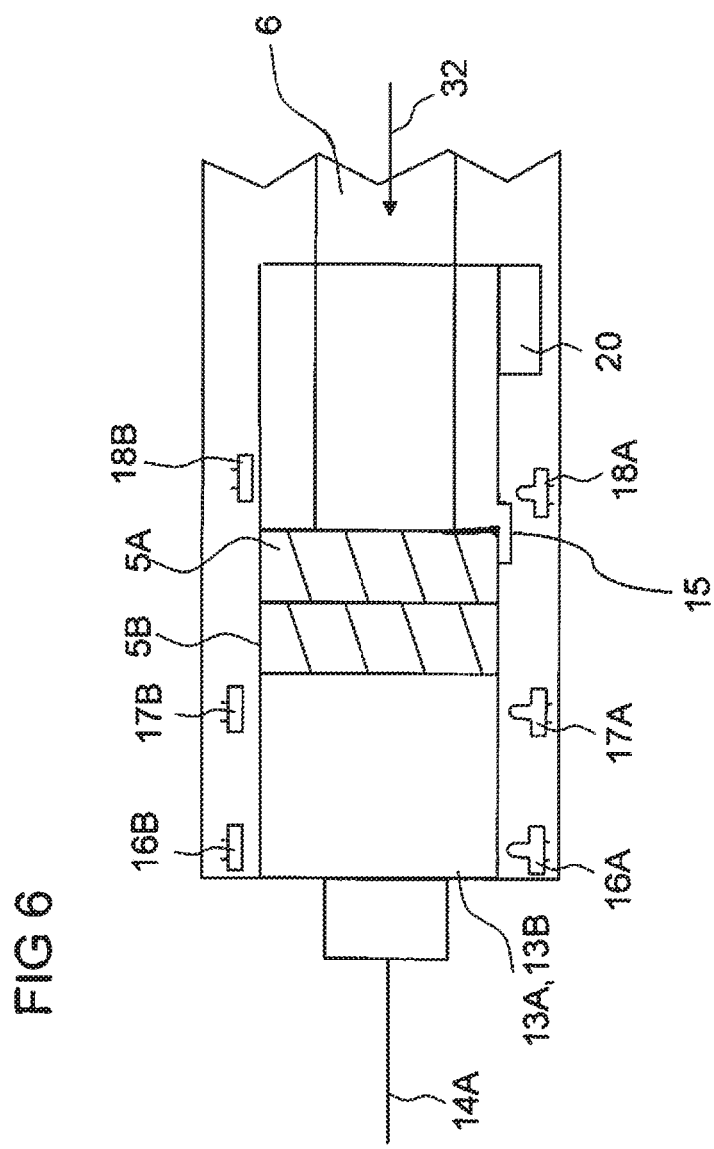

DRUG DELIVERY DEVICE AND METHOD FOR A DRUG DELIVERY DEVICE

CROSS REFERENCE TO RELATED APPLICATIONS

The present application is a continuation of U.S. patent application Ser. No. 15/350,587, filed Nov. 14, 2016, which is a continuation of U.S. patent application Ser. No. 13/883, 391, filed May 3, 2013, now U.S. Pat. No. 9,492,620, which is a U.S. National Phase Application pursuant to 35 U.S.C. § 371 of International Application No. PCT/EP2011/069815 filed Nov. 10, 2011, which claims priority to European Patent Application No. 10190936.4 filed Nov. 12, 2010 and U.S. Provisional Patent Application No. 61/438,406 filed Feb. 1, 2011. The entire disclosure contents of these applications are herewith incorporated by reference into the present application.

FIELD OF DISCLOSURE

This disclosure relates to a drug delivery device and to a method for a drug delivery device.

BACKGROUND

In a drug delivery device, often, a bung is provided within a container or cartridge that contains a product. The bung is displaced with respect to the container for delivering a dose of the product.

A drug delivery device is described in document EP 1 923 083 A1, for example.

SUMMARY

It is an object of the present disclosure to facilitate provision of a novel, preferably an improved, drug delivery device, for example a device providing high safety for a user.

This object may be achieved by the subject matter of the independent claims. Further features and advantageous embodiments are the subject matter of the dependent claims.

According to one aspect, a drug delivery device is provided. The drug delivery device may comprise a container. The container may be a cartridge. The device may comprise two or more products. The drug delivery device may comprise a first product. The drug delivery device may comprise a second product. The device may be configured to mix the first product and the second product with each other within the container for forming a drug mixture. The device may be configured for dispensing the drug mixture. The device may be switchable from a first state into a second state. In the first state, the first product and the second are expediently separated. In the second state, the first product and the second product may be mixed, thus forming the drug mixture. The drug delivery device may further comprise a mixing member. The mixing member may be configured to exert a force onto the container in order to move the container, preferably to mix the first product and the second product with each other.

In the first state, the device, in particular the container, comprises at least two separated, in particular unmixed, products. Due to the force exerted by the mixing member, the first product and the second product may be mixed such that, in the second state, the device, in particular the container, does no longer comprise two separated products but comprises only one mixed product, i.e. the drug mixture of the two products which is to be dispensed from the device.

According to an embodiment, the container comprises at least two retaining sections. The respective retaining section may comprise a chamber. The number of retaining sections may correspond to the number of, in particular separated, products held in the container in the first state of the device. In the first state, a first retaining section may hold the first product. In the first state, a second retaining section may hold the second product. The first retaining section and the second retaining section and, thus, the first product and the second product, may, in the first state, be separated from one another by means of a separating member. The separating member may be adapted and arranged to prevent fluid communication between the first retaining section and the second retaining section when the device is in the first state. The separating member may be moveable, preferably axially moveable, with respect to the container when switching the device from the first state into the second state.

The first product and the second product may be mixed within the second retaining section. The second retaining section may be a mixing chamber. In the first state, the first product and the second product may be separated, in particular they may be prevented from being mixed with one another, by means of the separating member. For mixing the first product and the second product, the separating member may be moved such that fluid communication between the first retaining section and the second retaining section is established, thus allowing the first product and the second product to be mixed with one another.

According to an embodiment, the container comprises a bypass. The bypass may be adapted and arranged to enable fluid communication between the first retaining section and the second retaining section. The bypass is expediently, in particular temporarily, opened when the separating member is moved with respect to the container when the device is switched from the first state into the second state.

The bypass may be closed, e.g. by means of the separating member, when the device is in the first state. The bypass may be closed when the device is in the second state. Accordingly, in the first state and in the second state, the second retaining section, in particular a proximal end of the second retaining section, may be sealed fluid-tightly, thus preventing unintentional flow of the respective product or the drug mixture into or out of the second retaining section.

According to an embodiment, a bung is moveably retained within the container. A proximal end of the first retaining section may be formed, in particular sealed fluid-tightly, by the bung. In the first state, a distal end of the first retaining section may formed, in particular sealed fluid-tightly, by the separating member. For switching the device from the first state into the second state, the bung may be moved with respect to the container. The device may be configured to transfer a movement of the bung into movement of the separating member with respect to the container to open the bypass.

According to an embodiment, when the bypass is opened, the bung may be configured to force the first product out of the first retaining section. The first product may be forced from the first retaining section via the bypass and into the second retaining section by means of the bung which is moved with respect to the container. The bung may be displaceable with respect to the separating member, thereby reducing the volume of the first retaining section. The bung may be moved relative to the separating member until the bung abuts the separating member.

Movement of the bung and, hence, of the separating member with respect to the container may cause the bypass to be opened and, thus, to enable flow of the first product out of the first retaining section. When flow of the first product out of the first retaining section is enabled, the bung may be moved with respect to the separating member. When the first product has been forced completely out of the first retaining section, the bung, in particular a distal end face of the bung may abut the separating member, in particular a proximal end face of the separating member. Accordingly, in the second state, the container comprises only the mixing chamber or the second retaining section. When the bung abuts the separating member, the bypass may be closed, e.g. by the bung. Unintentional flow of the first and/or the second product out of the second retaining section may thus be prevented.

According to an embodiment, the container comprises an inner surface. The inner surface may comprise a profile which is rotationally asymmetrical.

The profile may comprise a broken rotational symmetry. The container, in particular the inner surface of the container, may not be projected upon itself upon rotation of the container about an arbitrary angle with respect to a main longitudinal axis of the container. The rotational asymmetry may be configured to cause turbulences in at least one of the products when the container is moved in order to mix the first product and the second product. This may help to facilitate mixing of the products.

According to an embodiment, the device comprises a measuring unit. The measuring unit may be configured to determine whether the device is in the second state, i.e. whether the first product and the second product have been mixed to form the drug mixture. Additionally or alternatively, the measuring unit may be configured to determine a value of a parameter of the drug mixture when the device is in the second state.

The parameter may be indicative for a property of the drug mixture. The measuring unit may help to ensure that the device and, in particular, the drug mixture is ready for delivery when the device is in the second state. In this way, dispensing of a not correctly and/or not completely mixed drug mixture may be prevented. User safety may be increased.

According to an embodiment, the device comprises a housing. The measuring unit may be configured to determine a position of the separating member and/or the bung and, hence, of the container with respect to the housing.

According to an embodiment, the device comprises a control unit. The control unit may be configured to control the device. The control unit may be configured to store a predetermined value, in particular a predetermined range of values of a parameter of the drug mixture. Said parameter may be indicative for the property of the drug mixture. Furthermore, the control unit may be configured to compare the determined value of the parameter with the stored range of values. Furthermore, the control unit may be configured to control the state of the device, e.g. to control whether the device is in the first state or in the second state, dependent on the result of the comparison of the determined value with the predetermined range of values.

Depending on the value determined by the measuring unit, the control unit may automatically control the state of the device. User-operated steps for controlling the device and/or for controlling the property of the drug mixture may be redundant.

According to an embodiment, the measuring unit comprises at least one of, preferably a plurality of sensors. The sensors may be disposed at different positions along the container. The sensors may comprise optical and/or electronic, in particular opto-electronic, sensors.

The sensors may be provided individually or in a sensor array, the array comprising a plurality of sensors. The sensors may be configured to collect information about at least one property, e.g. a cloudiness, of the drug mixture. By means of the collected information, the measuring unit may automatically determine whether the drug mixture is ready to be dispensed or not, for example. User operated steps for determining whether the drug mixture is ready or not may be redundant.

According to an embodiment, when the device is in the second state, the control unit may be configured to determine whether the drug mixture fulfills requirements for being dispensed from the device, e.g. whether the first product and the second product have been mixed properly. When the value of the parameter determined by the measuring unit lies within the predetermined range of values, the drug mixture may be ready to be dispensed from the device. The control unit may be configured to cause the device to be in a ready-to-dispense mode. When the value is out of the predetermined range of values, the drug mixture may not be ready for being dispensed. Accordingly, the control unit may be configured to cause the device to be switched into a hold mode.

The measuring unit may be adapted and arranged to repeatedly, i.e. after a predetermined period of time, or continuously determine the value of the parameter. Accordingly, the control unit may be adapted and arranged to repeatedly or continuously control the property of the drug mixture and correspondingly to signal to the device whether it is in the ready-to-dispense mode or in the hold mode. Accordingly, the control unit may automatically determine and signal, whether the drug mixture is ready to be dispensed or not. Additionally, the device, in particular the control unit, may be configured to indicate to a user whether the device is in the ready-to-dispense mode or in the hold mode.

According to an embodiment, when the value of the parameter is out of the predetermined range of values, the control unit may be configured to cause the mixing member to exert force onto the container. Accordingly, when the value is out of the predetermined range, the container holding the drug mixture may be moved with respect to the housing for mixing the drug mixture. The drug mixture may be mixed until the value is again in the predetermined range before the device may then be switched from the hold mode into the ready-to-dispense mode.

Due to repeated mixing of the drug mixture, in particular mixing of the drug mixture when the value is out of the predetermined range, the measuring unit and the control may ensure automatically that the drug mixture fulfils requirements for being dispensed, e.g. that the value of the parameter is within the predetermined range, the drug mixture thus being mixed properly. Dispensing of a not correctly drug mixture may be prevented in this way. This may help to increase user safety.

According to an embodiment, the device comprises a user interface. The user interface may be adapted and arranged to indicate to a user whether the device is in the ready-to-dispense mode or in the hold mode. The user interface may be controlled by the control unit.

In this way, the user may be informed at any time, whether the drug mixture is ready for being dispensed or not. In this way, provision of a user friendly drug delivery device is facilitated.

According to an embodiment, device comprises an internal power supply, e.g. a battery. The internal power supply may be configured to supply power to the control unit and/or the user interface, for example.

According to an embodiment, the device comprises a timer. The timer may be configured to cause the mixing member to move the container for mixing the drug mixture after a predetermined period of time when the device is in the second state. Additionally or alternatively, the timer may be configured to cause the mixing member to move the container for mixing the drug mixture for a predetermined period of time when the device is in the second state.

Accordingly, when the device is in the second state, the timer may ensure a repeated mixing of the drug mixture. The predetermined period, in particular the time interval between two subsequent mixing operations, may be chosen, in particular may be measured empirically, such that the drug mixture may be ready to be dispensed from the device at any time.

According to an embodiment, time for mixing is a predetermined value stored in the device, in particular by the control unit of the device.

The time for mixing the drug mixture may be measured empirically.

According to an embodiment, when the device is in the second state, the measuring unit may be configured to determine whether the device has to be primed or nor. When the device has to be primed, a volume of the second retaining section is greater than the volume of the drug mixture.

Apart from the drug mixture, the second retaining section may comprise air, for example. Said air may help to facilitate mixing of the first product and the second product. Said air has to be removed, i.e. the device has to be primed, before a first dose of the drug mixture can be dispensed from the device.

According to an embodiment, the first product is a fluid product. The second product may be a fluid product or a solid product. The drug mixture to be dispensed from the device may comprise an emulsion, a solution or a suspension of the first product and the second product.

Accordingly, the device may be suited to dispense different kinds of drug mixtures, thus being able to meet the individual requirements of the user. The first product may be incompressible. Accordingly, movement of the bung with respect to the container for switching the device from the first state into the second state may be transferred to the separating member via the incompressible, e.g. fluid, first product.

A further aspect relates to a method for maintaining a predetermined property of a drug mixture which is to be dispensed from a drug delivery device. The method may comprise the step of providing a container for the drug delivery device. The container may be configured to hold the drug mixture. The method may comprise the step of, e.g. continuously or repeatedly, determining a value of a parameter of the drug mixture. The parameter may be indicative for the property of the drug mixture. The method may comprise the step of, continuously or repeatedly, determining whether said value lies within a predetermined range of values. The method may further comprise the step of exerting force onto the container to move the container and the drug mixture if the value is out of the predetermined range of values.

The value indicative for the property may be, preferably continuously, compared with the values lying within the predetermined range. Accordingly, there may be a continuous surveillance whether the drug mixture is ready for being dispensed from the device or not. If the drug mixture is not ready for being dispensed, the drug mixture may be moved, in particular mixed, thus ensuring that the value lies within the predetermined range, the drug mixture thus being ready to be dispensed from the device. In this way, it may be guaranteed automatically that the drug mixture comprises the predetermined property.

According to a preferred embodiment, a drug delivery device is provided comprising a container, a first product and a second product. The device is configured to mix the first product and the second product with each other within the container for forming a drug mixture and the device is further configured for dispensing the drug mixture. The device comprises a mixing member. The device is switchable from a first state, in which the first product and the second product are separated, into a second state, in which the first product and the second product are mixed. The mixing member is configured to exert a force onto the container in order to move the container to mix the first product and the second product with each other.

The mixing member may be suited to form the drug mixture in an automatic fashion. User-operated steps for mixing the first product and the second product may be redundant. This may help to reduce the error-proneness of the mixing operation.

According to a preferred embodiment, a method for maintaining a predetermined property of a drug mixture to be dispensed from a drug delivery device is provided comprising the following steps:

providing a container for the drug delivery device, the container being configured to hold the drug mixture, determining a value of a parameter of the drug mixture and determining whether said value lies within a predetermined range of values, exerting force onto the container to move the container and the drug mixture if the value is out of the predetermined range of values.

In this way, it may be ensured automatically, that the value is kept within the predetermined range of values. Accordingly, it may be guaranteed that the drug mixture is almost always ready to be dispensed from the device. Dispensing of a drug mixture with a value out of the predetermined range, in particular of a not correctly mixed drug mixture, may be prevented in this way. User safety may thus be increased.

A drug delivery device according to present disclosure may be configured for continuous surveillance whether the drug mixture is ready for being dispensed from the device or not. Therefore the device may comprise features as described above to enable the following functionalities:

The mixture may be monitored whether the drug mixture is ready for being dispensed from the device or not.

The mixture may be moved, shaken, vibrated or otherwise agitated when not ready for dispense or not in proper condition for dispense.

A sensor or sensor array may be configured to determine the proper condition by way of measuring the opacity, the cloudiness, the scattering or reflection, the transmission or the like values of a parameter indicative for the mixing property of the drug mixture.

Mixing or agitation should last until the mixture is in a condition or ready to be dispensed.

The end of mixing or agitation may be determined by either predefined values, e.g. a time interval, or alternatively by inspecting and/or monitoring the mixture during agitation.

The end of mixing or agitation may be determined by a predefined time value or alternatively by a value of a parameter, e.g. that is within a predetermined range of values.

The end of mixing or agitation may be determined by measuring a value of the opacity, cloudiness, scattering or reflection, or transmission or the like values of a parameter indicative for the mixing property of the drug mixture until the value lies within a predetermined range of values.

Mixing, agitation, or mixing operations may be repeated, e.g. after a time interval has lapsed or based on a value of a parameter indicative for the mixing property.

Repeating mixing, agitation, or mixing operations may be determined by a predefined a value of a parameter indicative for the mixing property, e.g. that is not within a predetermined range of values.

A value for the time between subsequent mixing operations may be predefined, e.g. a time value based on experience and may be stored in a control unit.

A value for the time between two subsequent mixing operations may be predefined and may be stored in a control unit.

A value for the number of necessary mixing operations may be predefined and may be stored in a control unit.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

FIG. 1 schematically shows a schematic side view of an exemplary embodiment of a drug delivery device, FIG. 2 schematically shows parts of the drug delivery device of FIG. 1, FIG. 3 schematically shows parts of the drug delivery device of FIG. 2 while mixing the first product and the second product, FIG. 4 shows a graph for a value of a parameter of the drug mixture as a function of time, FIG. 5 shows a graph for a value of a further parameter of the drug mixture as a function of time, FIG. 6 schematically shows parts of the drug delivery device of FIG. 1 while dispensing the drug mixture.

Like elements, elements of the same kind and identically acting elements may be provided with the same reference numerals in the figures.

DETAILED DESCRIPTION

Figure 7B:
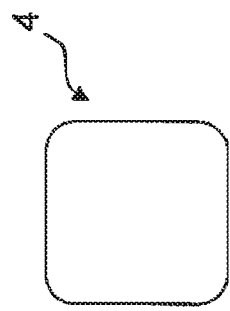
FIGS. 7A to 7E show embodiments of a container.

In FIG. 1 an exemplary embodiment of a drug delivery device 1 is shown. The drug delivery device comprises a housing 2. The drug delivery device 1 and the housing 2 have a distal end and a proximal end. The term "distal end" designates that end of the drug delivery device 1 or a component thereof which is or is to be arranged closest to a dispensing end of the drug delivery device 1. The distal end of the device 1 is indicated by arrow 11. The term "proximal end" designates that end of the device 1 or a component thereof which is or is to be arranged furthest away from the dispensing end of the device 1. The proximal end of the device 1 is indicated by arrow 12. The distal end and the proximal end are spaced apart from one another in the direction of an axis. The axis may be the main longitudinal axis 28 of the device 1 (see FIG. 3).

The drug delivery device 1 may comprise a cartridge holder 3. The cartridge holder 3 is, preferably releasably, secured to the housing 2. The device 1 comprises a container 4. The container 4 may be a cartridge. The container 4 is retained in the cartridge holder 3. The cartridge holder 3 stabilizes the container 4 mechanically. Alternatively, the container 4 may be connected directly to the housing 2 (see, for example, FIG. 2). In this case, the cartridge holder 3 may be redundant.

The container 4 comprises two retaining sections 4A, 4B. The respective retaining section 4A, 4B may form a chamber of the container 4. According to this embodiment, the container 4 comprises a first chamber or retaining section 4A. The container 4 comprises a second chamber or retaining section 4B. Of course, the container 4 may comprise three or more retaining sections (not illustrated).

The first retaining section 4A is configured to hold a first product 13A. The first product 13A may comprise a first compound for a drug mixture. The first product 13A may be a fluid. The fluid may be incompressible. The second retaining section 4B is configured to hold a second product 13B. The second product 13B may comprise a second compound for a drug mixture 13A, 13B. The second product 13B may comprise a fluid or a solid product. Preferably, the second product 13B is a solid product. The second product 13B may be a powdery product. The number of retaining sections may correspond to the number of products held in the container 4 in an initial state of the device 1, e.g. after assembly of the device for after inserting the container 4 into the device 1.

In a first state, e.g. the initial state, the first product 13A and the second product 13B may be separated, in particular unmixed. The first product 13A and the second product 13B are configured to be mixed for forming a drug mixture 13A, 13B which is to be dispensed from the device 1. When the first product 13A and the second product 13B are mixed, the device 1 may be in a second state.

Mixing of the products 13A, 13B may be performed in the second retaining section 4B, which is explained later on in more detail. The second retaining section 4B may be a mixing chamber of the container 4. Alternatively, a separate mixing chamber may be provided (not illustrated).

The term "first product", "second product" and/or "drug mixture", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The two retaining sections 4A, 4B holding the first product 13A and the second product 13B are separated fluid-tightly from one another by means of a separating member 5B when the device 1 is in the first state. In particular, the separating member 5B may seal the second retaining section 4B proximally when the device 1 is in the first state. By means of the separating member 5B, an unintentional mixing of the first product 13A and the second product 13B is prevented.

The separating member 5B is axially moveable, in particular in the distal direction, with respect to the container 4, e.g. when the device 1 is switched from the first state into the second state which is explained later on in more detail.

The device 1 comprises a bypass 15. The bypass 15 may comprise an indentation of the inner surface of the container 4. The bypass 15 is configured to enable mixing of the first product 13A and the second product 13B for switching the device 1 from the first state into the second state. In particular, when opened, the bypass 15 is adapted and arranged to provide fluid communication between the first retaining section 4A and the second retaining section 4B. When opened, the bypass 15 may enable flow of the first drug 13A out of the first retaining section 4A into the second retaining section 4B.

In the first state of the device 1, the bypass 15 may be closed, e.g. by means of the separating member 5B which prevents the first product 13A from entering the bypass 15. The separating member 5B may be arranged proximally with respect to the bypass 15 for this purpose. In the second state of the device 1, the bypass 15 may be closed as well. Accordingly, in the first state and in the second state, unintentional movement of the respective product 13A, 13B out of the respective chamber 4A, 4B may be prevented. The bypass 15 may be temporarily opened, e.g. by means of the separating member 5B moving with respect to the container 4, for switching the device 1 from the first state into the second state, which is explained later on in more detail.

The container 4 comprises an outlet 8. The drug mixture 13A, 13B (see FIG. 3) can be dispensed from the container 4 through the outlet 8. The outlet 8 is covered by a membrane 9. The membrane 9 may protect the drug mixture 13A, 13B against external influences during storage of the container 4. The membrane 9 may seal the outlet 8 fluid-tightly.

The drug delivery device 1 comprises a needle assembly 14, comprising a needle 14A. The needle assembly 14 may be releasably attached to the cartridge holder 3, for example by means of a thread. The needle 14A may be in fluid communication with the interior of the container 4.

The drug delivery device 1 comprises a bung 5A. The bung 5A is moveably retained in the container 4. The bung 5A is arranged in the proximal end section of the first retaining section 4A when the device 1 is in the first state (FIG. 1). In particular, the bung 5A seals the container 4, in particular the first retaining section 4A, proximally, when the device 1 is in the first state.

The device 1 comprises a pressure forming element 6, e.g. a piston rod. The device 1 comprises a drive mechanism 21. The drive mechanism is arranged at least partly within the housing 2 of the drug delivery device 1. The drive mechanism comprises a dose button 10 which may be actuatable for setting and/or injecting the dose. The drive mechanism 21 is configured to drive the pressure forming element 6 in the distal direction with respect to the container 4. Movement of the pressure forming element 6 in the distal direction may cause a dose of the drug mixture 13A, 13B to be dispensed from the container 4 (see FIG. 6).

The drug delivery device 1 may be an injection device. The drug delivery device 1 may be a pen-type device, in particular a pen-type injector. The device 1 may be a disposable or a re-usable device. The device 1 may be configured to dispense fixed doses of the drug mixture 13A, 13B, in particular doses the size of which may not be varied by the user, or variable, preferably user-settable, doses of the drug mixture 13A, 13B.

The drug delivery device 1 may be a manually driven device. Alternatively, the drug delivery device 1 may be an electrically driven device 1, as shown in FIG. 1. The device 1 may be a multi-dose device, in particular a device 1 configured to dispense a plurality of doses of the drug mixture 13A, 13B.

The device 1 may comprise a switch 22 for switching the device 1 on or off. According to this embodiment, mixing of the products 13A, 13B as well as setting and/or delivering a dose of the drug mixture 13A, 13B may be actuatable only if the device 1 is switched on by means of switch 22.

FIG. 2 schematically shows parts of the drug delivery device of FIG. 1.

FIG. 3 schematically shows parts of the drug delivery device of FIG. 2 while mixing the first product and the second product.

FIG. 4 shows a graph for a value of a parameter of the drug mixture as a function of time.

FIG. 5 shows a graph for a value of a further parameter of the drug mixture as a function of time.

For obtaining the drug mixture 13A, 13B, i.e. for switching the device 1 from the first state into the second state, the user may switch on the device 1. The mixing action may be initiated by actuation of a button of the device 1. For example, the dose button 10 may be used for this purpose. The pressure forming element 6 may be driven in the distal direction with respect to the container 4 by means of the drive mechanism 21. Thereby, the bung 5A is moved distally, thus exerting force onto the first, preferably fluid, product 13A. Due to the force exerted, the separating member 5B is moved in the distal direction with respect to the container 4 (see FIG. 2). In other words, movement of the bung 5A in the distal direction is transferred to the separating member 5B.

When the separating member 5B is moved distally, the separating member 5B passes the axial position of the bypass 15, e.g. the indentation, thus opening the bypass 15 (see FIG. 2). Fluid communication between the first retaining section 4A and the second retaining section 4B is thus established. When the bung 5A is moved further distally, the first product 13A is forced out the first retaining section 4A via the bypass 15 and into the second retaining section 4B. When the bypass 15 was opened, the bung 5A moves with respect to the separating member 5B, i.e. the distance between the bung 5A and the separating member 5B is reduced. Accordingly, the volume of the first retaining section 4A is reduced.

The bung 5A, driven by the pressure forming element 6, is moved distally until the first retaining section 4A is emptied, i.e. until the whole amount of the first product 13A has been forced out of the first retaining section 4A. When the first retaining section 4A was emptied, a distal end face of the bung 5A may abut a proximal end face of the separating member 5B (see FIG. 2). When the distal end face of the bung 5A abuts the proximal end face of the separating member 5B, the separating member 5B may have passed the axial position of the bypass 15, the bypass 15 thus being closed. In particular, the separating member 5B may be arranged more distally than the bypass 15. Fluid communication between the first retaining section 4A and the second retaining section 4A may thus be no longer possible. Unintentional flow of the first 13A and/or the second product 13B or of the drug mixture 13A, 13B, when the device 1 is in the second state, out of the second retaining section 4B may thus be prevented.

The two products 13A, 13B are now both held in the second retaining section 4B. The second retaining section 4B, i.e. the mixing chamber in this embodiment, may be the only fluid-tight inner section of the container 4 still remaining when the bung 5A abuts the separating member 5B. However, the two products 13A, 13B may not yet be mixed well enough for forming the drug mixture 13A, 13B.

For mixing the two products 13A, 13B, the device 1 comprises a mixing member 20. The mixing member 20 is adapted and arranged to mix the two products 13A, 13B. The mixing member 20 is configured to exert a force onto the container 4, thereby agitating the products 13A, 13B for mixing said products 13A, 13B. The force may be an oscillating force, for example. The force may be directed longitudinally (see arrow 31 in FIG. 3), radially (see arrow 30 in FIG. 3) and/or angularly (see arrow 29 in FIG. 3) with respect to the main longitudinal axis 28. The force may be eccentrical with respect to the main longitudinal axis 28 and/or eccentrical with respect to a main longitudinal axis of the container 4.

Furthermore, the mixing member 20 may be configured to influence a mixing property of the drug mixture 13A, 13B, 13B, which is explained later on in more detail. The mixing member 20 may comprise a shaking mechanism, for example. The mixing member 20 may comprise a motor. The mixing member 20 may comprise a vibration accumulator, e.g. as often used in mobile phones. The mixing member 20 may transfer the force generated by the motor or vibration accumulator to the container 4.

The device 1 comprises a measuring unit 16, 17, 18. The measuring unit 16, 17, 18 is configured to monitor a position of the separating member 5B and/or the bung 5A and, thus, of the container 4 with respect to the housing 2. In this way, the measuring unit 16, 17, 18 may determine whether the container 4 was introduced properly into the device 1. Additionally or alternatively, the measuring unit 16, 17, 18 may determine whether the complete amount of the first product 13A was forced out of the first retaining section 4A, i.e. whether the bung 5A abuts the separating member 5B.

Additionally or alternatively, the measuring unit 16, 17, 18 may be configured to monitor a status of the mixing of the two products 13A, 13B, e.g. whether the products 13A, 13B have already been mixed or not, i.e. whether the device 1 was switched into the second state or not. Additionally, in the second state of the device 1, the measuring unit 16, 17, 18 is adapted and arranged to monitor a value 24, 36 (see FIGS. 4 and 5) of a parameter which is indicative for the mixing property of the drug mixture 13A, 13B. In this way, the measuring unit 16, 17, 18 may determine whether the drug mixture 13A, 13B is ready to be dispensed from the device 1 or not, which is explained later on in more detail. In particular, the measuring unit 16, 17, 18 may provide a quality control for the drug mixture 13A, 13B.

Additionally or alternatively, the measuring unit 16, 17, 18 may be configured to determine whether there is still drug mixture 13A, 13B, in particular at least one dose of the drug mixture 13A, 13B, remaining in the second retaining section 4B after a dose or a plurality of doses of the drug mixture 13A, 13B was dispensed from the device 1, which is described later on in more detail. This may be achieved by the determination of a load current, when the pressure forming element 6 is tried to be moved distally for dispensing a dose.

According to this embodiment, the measuring unit 16, 17, 18 comprises three light sources 16A, 17A, 18A. The respective light source 16A, 17A, 18A may be an LED, for example. Alternatively, the measuring unit 16, 17, 18 may comprise a light source array comprising a plurality of light sources. The light sources 16A, 17A, 18A are arranged at different positions along the container 4.

According to this embodiment, the measuring unit 16, 17, 18 comprises three sensors 16B, 17B, 18B. Alternatively, the measuring unit 16, 17, 18 may comprise a sensor array comprising a plurality of sensors. Using a respective array of light sources and sensors may be especially applicable for performing continuous measurements, e.g. for determining the continuous movement of the separating member 5B and/or the bung 5A with respect to the container 4.

Sensors 16B, 17B, 18B may be optical sensors, in particular opto-electronical sensors. Sensors 16B, 17B, 18B may be photodiodes, for example. The sensors 16B, 17B, 18B are arranged at different positions along the container 4. One respective sensor 16B, 17B, 18B may be configured to receive light previously emitted by one respective light source 16A, 17A, 18A. For this purpose, the respective sensor 16B, 17B, 18B and the respective light source 16A, 17A, 18B may be arranged at the same axial position with respect to the main longitudinal axis 28 but opposite to one another.

Sensors 16B, 17B, 18B may be adapted and arranged to perform transmission measurements. In particular, sensors 16B, 17B, 18B may be configured to receive radiation emitted by the light sources 16A, 17A, 18A and, afterwards, passed through the components of the device 1, e.g. the drug mixture 13A, 13B and to transform said radiation into electrical signals, e.g. transmission signals. For this purpose, sensors 16B, 17B, 18B and light sources 16A, 17B, 18A may be arranged at different sides of the container 4, as shown in FIG. 2, for example. Thus, the radiation has to pass through the whole container 4 before it can be received by the respective sensor 16B, 17B, 18B. Sensors 16B, 17B, 18B and associated light sources 16A, 17B, 18A may be arranged mirror-symmetrically with respect to the main longitudinal axis 28.

Alternatively, sensors 16B, 17B, 18B may be adapted and arranged to perform reflection measurements. In particular, sensors 16B, 17B, 18B may be configured to receive radiation previously emitted by the light sources 16A, 17A, 18A and reflected by components of the device 1, e.g. the container 4, the drug mixture 13A, 13B, the bung 5A and/or the separating member 5B and to transform said radiation into electrical signals, e.g. reflexion signals. For this purpose, the sensors 16B, 17B, 18B and the light sources 16A, 17A, 18A may be arranged beside one another and at the same side of the container 4 (not explicitly shown).

The information collected by the sensors 16B, 17B, 18B may be fed back to a control unit or processing unit 39, for example, to determine the axial position of the separating member 5B and/or to process the measured value 24 (see FIG. 4) of the parameter. The control unit 39 may be a control chip, for example. Functionality of the control unit 39 is explained later on in more detail.

When the complete amount of the first product 13A has been forced out of the first retaining section 4A, the control unit 39 may receive signals from the measuring unit 16, 17, 18 indicating that the bung 5A abuts the separating member 5B. Accordingly, the control unit 39 may signal to the mixing member 20 to exert force onto the container 4 (see FIG. 3). Due to the force exerted by the mixing member 20, the container 4 and, thus, the first product 13A and the second product 13B, are moved with respect to the housing 2 for mixing the first product 13A and the second product 13B. In particular the products 13A, 13B may be shaken. The container 4 and/or the device 1 may vibrate due to the force exerted by the mixing member 20, for example.

The volume of the second retaining section 4B is preferably greater than the volume of the first product 13A and the second product 13B combined and, in particular, of the drug mixture 13A, 13B. In particular, the second retaining section 4B may retain air. The more space there is available in the second retaining section 4B, the more the mixed products 13A, 13B may be moved. Thus, if there is air present, the mixing of the products 13A, 13B may be improved, as more movement usually improves or accelerates the mixing. Of course, said air should be removed from the container 4 before a first dose of the drug mixture 13A, 13B is dispensed from the device 1, i.e. the device 1 should be primed, which is explained later on in more detail.

Figure 7E:
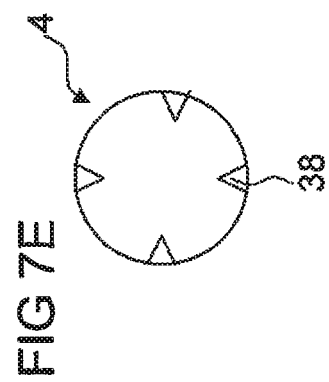
Figure 7D:
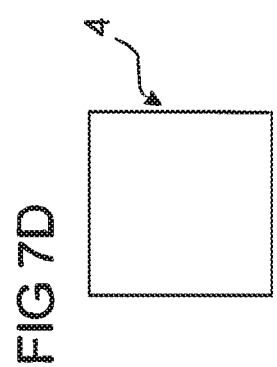
Figure 7A:
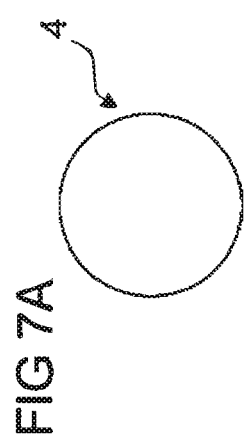

Furthermore, the mixing may be influenced by the shape of the container 4 and/or a structure of an inner surface of the container 4. The container 4 may comprise a circular cross section (see FIG. 7A). Alternatively, the inner surface may be rotationally asymmetric. In this context, the term "rotationally asymmetric" preferably means that the container 4 is not projectable upon itself upon rotation of the container 4 about an arbitrary angle with respect to the main longitudinal axis 28.

Figure 7C:
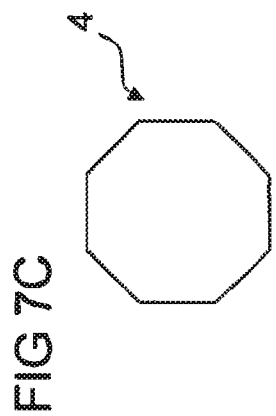

The inner surface of the container 4 may comprise a profile having a broken rotational symmetry with respect to the main longitudinal axis 28. Due to the broken rotational symmetry the mixing operation may be optimized, e.g. the mixing time may be minimized. For example, the container 4 may comprise a rectangular (see FIG. 7D) or hexagonal cross section (see FIG. 7C). Alternatively, the container 4 may comprise a quadratic cross section, for example a cross section with rounded edges (see FIG. 7B). Additionally or alternatively, the container 4, in particular the inner surface of the container 4, may comprise features 38 protruding radially inwardly from the inner wall (see FIG. 7E). In these cases, the cross section of the pressure forming element 6 had to be adjusted to the cross section of the container 4. The rotational asymmetry of the inner surface may cause turbulences in the fluid product, e.g. the first product 13A, when the container 4 is moved to mix the first product 13A and the second product 13B. This may help to facilitate mixing of the products 13, 13B.

In case the second product 13B is solid, the drug mixture 13A, 13B may comprise a suspension or solution. In case the second product 13B comprises a fluid, the drug mixture 13A, 13B may comprise a solution or an emulsion. The drug mixture 13A, 13B may be a reaction product of the products. Alternatively, the drug mixture 13A, 13B may not comprise a reaction product.

After a predetermined period of time, i.e. the mixing time, which may be determined in empirical measurements and which may be stored in the control unit 39, for example, the control unit 39 may switch off mixing member 20. The device 1 may now be in the second state.

Mixing of the two products 13A, 13B and, hence, the property of the drug mixture 13A, 13B may be subject to variations or may even fail as the mixing depends on different quantities, e.g. the time for the mixing, the proportion of the first product 13A and the second product 13B, the solubility of the respective product 13A, 13B.

Said quantities may at least partly be determined from empirical measurements. For example, the property of the drug mixture 13A, 13B may vary with increasing time which has passed since the products 13A, 13B were mixed. Accordingly, after having mixed the first product 13A and the second product 13B, it has to be ensured that the drug mixture 13A, 13B is ready to be dispensed. The quantities influencing the mixing property, e.g. the time for the mixing and/or the time between two mixing operations, may be tested in the laboratory and may be, together with a safety factor, stored in a software, e.g. the control unit 39, to enable a quality control of the drug mixture 13A, 13B.

When the device 1 is in the second state, the measuring unit 16, 17, 18, in particular sensors 16B, 17B, 18B, may collect information for determining the value 24, 36 of at least one parameter which is indicative for the mixing property of the drug mixture 13A, 13B, e.g. a quality control is performed by means of the measuring unit 16, 17, 18. The parameter indicative for the property of the drug mixture 13A, 13B may be the cloudiness of the drug mixture 13A, 13B and/or the transition of clear, in particular unmixed products 13A, 13B into, for example, a blue drug mixture 13A, 13B in case the drug mixture 13A, 13B is a suspension.

The value 24, 36 for the parameter may, for example, be the transmission-signal of light, which was emitted by a respective light source 16A, 17A, 18A, afterwards passing through the drug mixture 13A, 13B. Said transmission may give hint on the cloudiness of the drug mixture 13A, 13B and hint on the mixing quality of a suspension, for example. The information collected, e.g. the transmission and/or reflexion signals (see FIGS. 4 and 5), may be signalled to the control unit 39.

The control unit 39 may be configured to store a predetermined range 33, 37 of values of the parameter indicative for the property of the drug mixture 13A, 13B. Furthermore, the control unit 39 is configured to compare the value 24, 36 of the parameter determined by the measuring unit 16, 17, 18 with the stored predetermined range 33, 37 of values. In this way, the control unit 39 may control the state of the device 1 dependent on the result of the comparison of the determined value 24, 36 with the predetermined range 33, 37 of values, which is explained in more detail later on.

The control unit 39 may determine, whether value 24, 36 lies within the predetermined range 33, 37 of values (FIGS. 4 and 5). The predetermined range 33, 37 of values may be determined in empirical measurements, for example. Said empirical measurements could comprise the determination of the characteristic transmission of light passing a suspension, for example.

For example, the respective sensor 16B, 17B, 18B may receive a high transmission signal S in case of a clear fluid, e.g. the unmixed first product 13A. In case of a suspension of the first product 13A and the second product 13B which is ready for being dispensed, the transmission signal S may be small, indicating that a blurring of the mixed product has occurred, e.g. that the first product 13A and the second product 13B have been mixed properly (see FIG. 4). In case that the second product 13B is soluble, the respective sensor 16B, 17B, 18B may be configured to determine a transmission signal in dependence of a coloration of the mixed product 13A, 13B. The two products 13A, 13B may be configured such that, if the two products 13A, 13B are mixed and form a solution, the colour of the drug mixture 13A, 13B changes such as compared to the fluid product(s) when the two products 13A, 13B were separated from each other. The greater the coloration, the smaller the transmission signal S (see FIG. 4). When the transmission signal S is small, the two products 13A, 13B may be mixed properly and the drug mixture 13A, 13B may be ready to be dispensed from the device 1.

As shown in FIG. 4, within a first time interval 25, the value 24 for the transmission signal S is high. The first product 13A and the second product 13B may not be mixed properly. In the first time interval 25, value 24 may be out of the predetermined range 33. If value 24 is out of the predetermined range 33, the drug mixture 33 may not be ready for being dispensed. Accordingly, the device 1 may be switched into a hold mode by means of the control unit 39.

In FIG. 4, after the first time interval 25, e.g. a mixing time of five minutes, the value 24 may lie within the range 33. When the value 24 is within the predetermined range 33, e.g. the transmission signal S is small, the drug mixture 33 may be ready for being dispensed, i.e. the drug mixture 13A, 13B may have the predetermined property. Thereafter, within a given second time interval 26, which may be determined from empirical values, the drug mixture 13A, 13B may be ready for being dispensed from the device 1. In this case, the device 1 may be switched into a ready-to-dispense mode by means of the control unit 39.

Alternatively, the respective sensor 16B, 17B, 18B may collect information about the solid product, e.g. the second product 13B. For example, as shown in FIG. 5, when the first product 13A and the second product 13B are unmixed then, in a first time interval 34, the value 36 for the transmission signal S may be small, indicating that the second product 13B has not yet been mixed with, e.g. dissolved in, the first product 13A. After a given time interval, e.g. the first time interval 34, the first product 13A and the second product 13B may have been mixed such that that value 36 for the transmission is high and lies within the predetermined range 37. Accordingly, a suspension or solution of the first product 13A and the second product 13B may have been obtained and the mixed drug 13A, 13B may be ready to be dispensed. The device 1 may be switched into the ready-to-dispense mode by means of the control unit 39.

Alternatively to the depicted transmission measurements, the respective sensor 16B, 17B, 18B may collect information about the reflexion of radiation emitted by the respective light source 16A, 17A, 18A (not explicitly shown). In the case when the respective sensor, e.g. sensor 16B, collects information about the solid product, a small value 36 for the reflexion signal in FIG. 5 would indicate, that a solution or suspension of the first product 13A and the second product 13B has been obtained. The device 1 may be switched into the ready-to-dispense mode by means of the control unit 39. After the time interval 34, the value 36 may be high indicating a strong reflexion of light and, hence, that the first product 13A and the second product 13B have been unmixed, i.e. that the respective sensor 16B, 17B, 18B receives light reflected only by the solid, e.g. second, product 13B. Accordingly, after time interval 34, e.g. after one hour after the mixing operation, the value 36 may be out of the predetermined range 37 (not explicitly shown in FIG. 5) and the device 1 may be switched into the hold mode by means of the control unit 39.

When value 24, 36 is out of the predetermined range 33, 37 the control unit 39 may be configured to send a signal to the mixing member 20. In particular, the mixing member 20 may be switched on by means of the control unit 39. Accordingly, the mixing member 20 may exert force onto the container 4 and, thus, onto the drug mixture 13A, 13B to mix the drug mixture 13A, 13B. The drug mixture 13A, 13B may be mixed until the value 24, 36 is again in the predetermined range 33, 37. In the hold mode, determining value 24, 36 by means of the measuring unit 16, 17, 18 may, for example, occur continuously for ensuring that the mixing member 20 is switched on until value 24, 36 is again within the predetermined range 33, 37 of values. In the ready-to-dispense mode, determining value 24, 36 may, for example, occur repeatedly after given, e.g. empirical determined, time intervals have lapsed.

Alternatively, the mixing operation may be an iterative process. In particular, the control unit 39 may operate without an empirical value or a range 33, 37 of values for the parameter indicative for the property of the drug mixture 13A, 13B. In this case, the first product 13A and the second product 13B may be mixed by means of the mixing member 20 as described above. Afterwards, the measuring unit 16, 17, 18 may determine the value 24, 36 of the parameter which may be signalled to the control unit 39. The control unit 39 may be configured to store and control said value 24, 36. A predetermined value for the mixing time and/or for the time between two subsequent mixing operations and/or the number of necessary mixing operations may be stored in the control unit 39. Depending on the values stored, the control unit 39 may actuate the mixing member 20 to mix the drug mixture 13A, 13B for obtaining a drug mixture 13A, 13B which is ready to be dispensed from the device 1.

As described above, mixing of the first product 13A and the second product 13B and, in particular, the property of the drug mixture 13A, 13B, may depend for example on the amount of the respective product 13A, 13B, the mixing time, the time between two subsequent mixing operations and/or the solubility of the respective product 13A, 13B, e.g. of the solid product 13B. These quantities have to be adjusted, e.g. by gathering empirical values, for optimizing the mixing operation and, hence, the property of the drug mixture 13A, 13B. The empirical values may be stored by the device software, e.g. by the control unit 39.

The device 1 may comprise a user interface 19. The user interface 19 may be adapted and arranged to indicate to a user whether the drug mixture 13A, 13B is ready for being dispensed or not, i.e. whether the device 1 is in the ready-to-dispense mode or in the hold mode. User interface 19 may comprise a display. The user interface may comprise light emitting elements, such as a bulb, light sources, or the like. The light emitting elements may be configured to emit light of different colour for indicating the user the different states of the device 1. The device 1 may furthermore comprise an internal power supply 40, e.g. a battery for supplying power to the control unit 39 and the user interface 19.

When the value 24, 36 is within the predetermined range 33, 37 and/or when the control unit 39 has actuated the mixing member 20 to mix the drug mixture 13A, 13B for the predetermined period of time, for example, the control unit 39 may signal to the user interface 19 to display, for example, yellow light for indicating that the device 1 is in the ready-to-dispense mode, i.e. the drug mixture 13A, 13B is ready to be dispensed, the device 1 however not yet being primed, as explained later on in more detail. If value 24, 36 is out of the predetermined range 33, 37, and/or if the drug mixture 13A, 13B was not mixed for the predetermined period of time, the control unit 39 may signal to the user interface 19 to display red light for indicating that the device 1 is in the hold mode. In this way, the user may realize immediately, whether the first product 13A and the second product 13B have been mixed properly, the drug mixture 13A, 13B thus being ready to be dispensed or not.

Additionally or alternatively to the measuring unit 16, 17, 18, the device 1 may comprise a timer 23. When the device 1 is in the second state, the timer 23 may be configured to provide a signal to the control unit 39 to cause the mixing member 20 to move the container 4 for mixing the drug mixture 13A, 13B after a predetermined period of time and/or for a predetermined period of time. Accordingly, the timer 23 may ensure a repeated mixing of the drug mixture 13A, 13B. A determination of value 24, 36 by means of the measuring unit 16, 17, 18 may be redundant, in this case.

The predetermined period, in particular the time interval between two subsequent mixing operations and/or the mixing time, may be chosen such that the value 24, 36 is prevented from falling out of the range 33, 37. In this way, the timer 23 may ensure the drug mixture 13A, 13B to be ready for being dispensed from the device 1 at any instant. In other words, it may be guaranteed automatically, e.g. without the need of continuous determination of value 24, 36 by means of the measuring unit 16, 17, 18, that value 24 is always within the predetermined range 33, 37. The time interval may be determined empirically. For example, the time interval between two subsequent mixing operations may be taken from the average time which a suspension needs for becoming unmixed in case that the first product 13A is a fluid product and the second product 13B is a powdery product. This may be redundant for real solutions, e.g. in case that the first product 13A is a fluid product and the second product 13B is a fluid product, for example. These empirical values may be provided with a safety factor for obtaining a time interval between two mixing operations which ensures that the value 24, 36 is prevented from falling out of the range 33, 37.

When the user interface 19 provides yellow light, i.e. when the device 1 is in the ready-to-dispense mode, the drug mixture 13A, 13B may be ready to be dispensed from the device 1.

However, before a dose of the drug mixture 13A, 13B is to be dispensed to the user, remaining air in the second retaining section 4B has to be removed, i.e. the device 1 has to be primed. For this purpose, the user may turn around the device 1 such that air may be removed from the device 1 without wasting drug mixture 13A, 13B. Afterwards, the user may push onto the dose button 10 such that the pressure forming element 6 is slightly moved distally. Thereby, the separating member 5B and the bung 5A are moved distally for forcing the air out of the second retaining section 4B. When all air has been removed from the second retaining section 4B, which may also be determined by means of the measuring unit 16, 17, 18, e.g. by means of determining a value of a parameter which is indicative for the presence of air in the second retaining section 4B, the device 1 may be ready for injecting the first dose of the drug mixture 13A, 13B. The user interface 19 may now be signalled by the control unit 39 to provide green light, for example.

FIG. 6 schematically shows parts of the drug delivery device of FIG. 1 while dispensing the drug mixture.

For dispensing the drug mixture 13A, 13B, the user may actuate the dose button 10. Actuation of the dose button 10 may result in distal movement of the pressure forming element 6 (see arrow 32) which is driven by the drive mechanism 21. The pressure forming element 6 forces the bung 5A and the separating member 5B, which abuts the bung 5A, in the distal direction with respect to the container 4. When the bung 5A and the separating member 5B are moved distally, a dose of the drug mixture 13A, 13B is dispensed from the device 1.

Other implementations are within the scope of the following claims. Elements of different implementations may be combined to form implementations not specifically described herein.

The invention claimed is:

1. A drug delivery device, comprising:
   a container;
   a first product and a second product, the drug delivery device being configured to mix the first product and the second product with each other within the container for forming a drug mixture, and the drug delivery device being further configured for dispensing the drug mixture;
   a measuring unit; and
   a control unit,
   wherein the drug delivery device is switchable from a first state in which the first product and the second product are separated, into a second state in which the first product and the second product are mixed,
   wherein the measuring unit is configured to determine a value of a parameter of the drug mixture when the drug delivery device is in the second state,
   wherein the control unit is configured to determine whether the first product and the second product have been mixed properly when the drug delivery device is in the second state, and
   wherein the control unit is configured to prevent dispensing of an incorrectly and/or an incompletely mixed drug mixture.

2. The drug delivery device according to claim 1, wherein the value of the parameter of the drug mixture is indicative for a mixing property of the drug mixture.

3. The drug delivery device according to claim 1, wherein the drug delivery device is configured to perform a quality control via the measuring unit.

4. The drug delivery device according to claim 1, wherein the control unit is configured to determine whether the drug delivery device has to be primed.

5. The drug delivery device according to claim 4, wherein the value of the parameter of the drug mixture is indicative for the presence of air in the container.

6. The drug delivery device according to claim 1, wherein the control unit is configured to determine whether there is still drug mixture remaining in the container after a dose or a plurality of doses of the drug mixture have been dispensed from the drug delivery device.

7. The drug delivery device according to claim 6, wherein the value of the parameter of the drug mixture is indicative for the presence of the drug mixture in the container.

8. The drug delivery device according to claim 1, wherein the measuring unit is configured to repeatedly or continuously determine the value of the parameter of the drug mixture.

9. The drug delivery device according to claim 1, wherein the control unit is configured to switch the drug delivery device between a ready-to-dispense mode and a hold mode.

10. The drug delivery device according to claim 9, wherein the drug delivery device comprises a user interface adapted and arranged to indicate to a user whether the drug delivery device is in the ready-to-dispense mode or in the hold mode, and wherein the user interface is controlled by the control unit.

11. The drug delivery device according to claim 10, wherein the user interface comprises light emitting elements, the light emitting elements being configured to emit light of different colors that respectively correspond to different modes of the drug delivery device.

12. The drug delivery device according to claim 1, wherein the control unit is configured to:
  store a predetermined range of values of the parameter of the drug mixture;
  compare the determined value of the parameter of the drug mixture with the stored range of values; and
  control a state of the drug delivery device dependent on a result of a comparison of the determined value to the predetermined range of values.

13. The drug delivery device according to claim 12, wherein when the value of the parameter determined by the measuring unit lies within the predetermined range, the control unit is configured to cause the drug delivery device to be in a ready-to-dispense mode, and wherein when the value is out of the predetermined range, the control unit is configured to cause the drug delivery device to be switched into a hold mode.

14. The drug delivery device according to claim 12, wherein the measuring unit is configured to repeatedly or continuously determine the value of the parameter of the drug mixture, and wherein the control unit is configured to repeatedly or continuously determine whether the value lies within the predetermined range of values.

15. The drug delivery device according to claim 12, wherein the control unit is configured to prevent dispensing of the drug mixture when the determined value of the parameter of the drug mixture is outside of the predetermined range of values.

16. The drug delivery device according to claim 1, wherein the drug delivery device comprises a mixing member, and wherein the mixing member is configured to exert a force on the container in order to move the container to mix the first product and the second product with each other.

17. The drug delivery device according to claim 1, wherein the container comprises at least two retaining sections, wherein in the first state, a first retaining section holds the first product and a second retaining section holds the second product, and wherein the first retaining section and the second retaining section, in the first state, are separated from one another by a separating member which is adapted and arranged to prevent fluid communication between the first retaining section and the second retaining section, the separating member being moveable with respect to the container when switching the drug delivery device from the first state into the second state,
  wherein the container comprises a bypass adapted and arranged to enable fluid communication between the first retaining section and the second retaining section, wherein the bypass is opened when the separating member is moved with respect to the container when the drug delivery device is switched from the first state into the second state, and
  wherein a bung is moveably retained within the container, and wherein, in the first state, one end of the first retaining section is formed by the bung and another end is formed by the separating member, and wherein, for switching the drug delivery device from the first state into the second state, the drug delivery device is configured to transfer a movement of the bung to the separating member to open the bypass, wherein, when the bypass is opened, the bung is configured to force the first product out of the first retaining section, the bung being displaceable with respect to the separating member until the bung abuts the separating member.

18. The drug delivery device according to claim 1, wherein the first product is a fluid product and the second product is a fluid product or a solid product, and wherein the drug mixture comprises an emulsion, a solution, or a suspension.

* * * * *